(12) United States Patent
Majercak et al.

(10) Patent No.: US 8,454,535 B2
(45) Date of Patent: Jun. 4, 2013

(54) HIGHLY FLEXIBLE TUBULAR DEVICE FOR MEDICAL USE

(75) Inventors: David Christopher Majercak, Stewartsville, NJ (US); Daniel Olsen, Califon, NJ (US)

(73) Assignee: Cordis Corporation, Miami Lakes, FL (US)

( * ) Notice: Subject to any disclaimer, the term of this patent is extended or adjusted under 35 U.S.C. 154(b) by 50 days.

(21) Appl. No.: 12/696,296

(22) Filed: Jan. 29, 2010

(65) Prior Publication Data

US 2011/0190664 A1 Aug. 4, 2011

(51) Int. Cl.
*A61B 5/00* (2006.01)
*A61M 25/00* (2006.01)

(52) U.S. Cl.
USPC ............................................... 600/585

(58) Field of Classification Search
USPC ............... 600/101, 118, 139, 144, 433, 434, 600/585; 604/6.16, 7, 21, 93.01, 95.01, 103.01, 604/103.04, 164.13, 171, 264, 412, 508, 604/523

See application file for complete search history.

(56) References Cited

U.S. PATENT DOCUMENTS

| | | | |
|---|---|---|---|
| 6,107,004 A * | 8/2000 | Donadio, III | 430/320 |
| 7,520,863 B2 | 4/2009 | Grewe et al. | |
| 2008/0077085 A1 * | 3/2008 | Eidenschink et al. | 604/96.01 |
| 2010/0010526 A1 | 1/2010 | Mitusina | |

FOREIGN PATENT DOCUMENTS

| | | |
|---|---|---|
| WO | 03022162 A1 | 3/2003 |
| WO | 2007036815 A2 | 4/2007 |

* cited by examiner

*Primary Examiner* — Brian Szmal

(57) ABSTRACT

The invention relates to an elongated torque tube for use in medical applications. The torque tube comprises an elongated tubular structure having a cylindrical cross section and defining a longitudinal axis and a circumferential axis, the elongated tubular structure including a helical cut having a finite thickness and extending along the length of the elongated tubular structure, the helical cut being oriented along the circumferential axis and including a plurality of flexural units defined by discontinuous cuts aligned with the circumferential axis.

9 Claims, 4 Drawing Sheets

FIG. 4A
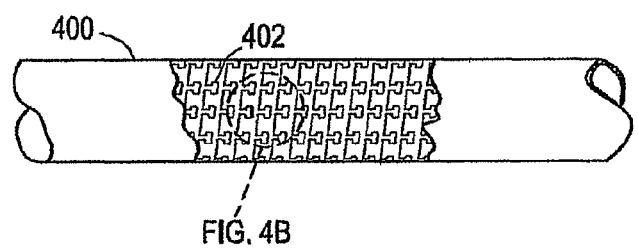
FIG. 4B
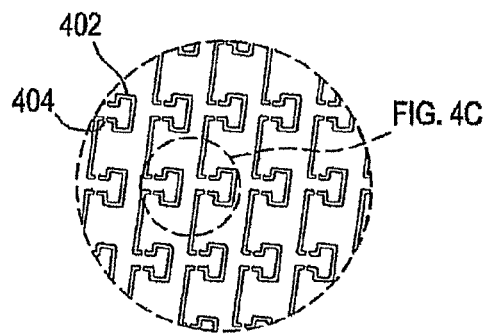
FIG. 4C
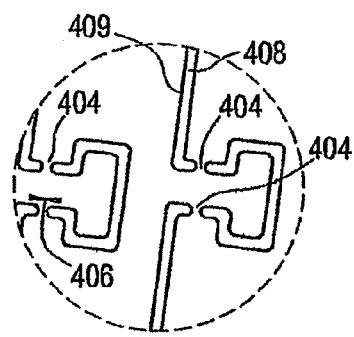
FIG. 5A  FIG. 5B  FIG. 5C  FIG. 5D
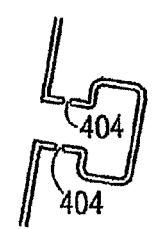 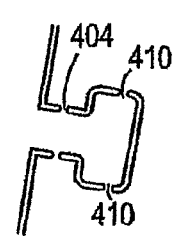 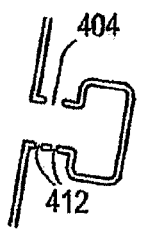 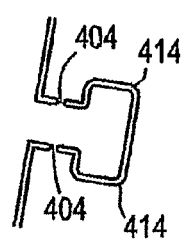

HIGHLY FLEXIBLE TUBULAR DEVICE FOR MEDICAL USE

BACKGROUND OF THE INVENTION

1. Field of the Invention

The present invention relates to tubular medical devices, and more particularly, to highly flexible, tubular medical devices such as catheters and guide wires having high initial torque transmission efficiencies.

2. Description of the Related Art

Intravascular catheters as well as other types of catheters are essential to the practice of modern interventional medicine. A catheter sheath introducer comprises three main components; namely a dilator, a cannula fitted with a hemostatic valve and a side port. Catheter sheath introducers allow guide wires and a variety of catheters to be safely introduced into the vasculature. There are many types of guide wires and catheters, including diagnostic catheters, guiding catheters, percutaneous transluminal angioplasty balloon catheters and self expanding stent delivery catheters. As stated herein there is a wide range of catheters that may be utilized in the vasculature or in virtually any other organ in the body that allows safe passage.

In a typical interventional arterial procedure, for example, stenting a stenotic region, a catheter sheath introducer is utilized to access a vessel that is of interest or will lead to the vessel of interest. Once access is achieved, a guide wire is inserted and moved through the vessel or vessels to the desired location, typically, distal to the treatment site. Once in position, various devices such as balloon catheters and balloon catheters with stents, may be introduced over the guide wire and moved into position at the desired location or treatment site.

U.S. Pat. No. 7,520,863 assigned to Cordis Corporation discloses a guide wire with a deflectable tip having improved torque characteristics. This patent illustrates the need to have a small diameter guide wire that includes a distal tip which may be deflected very precisely in either of two directions to enhance steerability. In particular, the guide wire comprises an elongated member formed with re-occurring steps, or step undulations, which is wound into a helical configuration so that adjacent turns can loosely interlock thereby preventing movement between adjacent turns. Such interlocking turns enhance the rotational rigidity or torquability of the coil such that when the proximal end of the coil is rotated, the distal end of the coil will eventually rotate also. Accordingly, the distal end of the coil more nearly tracks, rotationally, the proximal end of the coil.

In certain procedures, the vessel or vessels through which these elongated tubular devices have to be moved may be highly tortuous and/or highly angulated. Accordingly, the various devices that are inserted should preferably be flexible, steerable and pushable. These properties, as well as others, need to be balanced to create a device capable of traversing the most difficult pathways. In other words, it would be preferable to have a device that is flexible so that it may be steered through even the most tortuous pathway, but also rigid enough to be pushable to the desired location. In addition, physicians do not like a lack of high initial torque response. Basically, no physician engaging in an interventional procedure wants to make unnecessary movements. For example, when the physician wants to torque a guide wire in order to steer it, he or she wants an immediate response. More specifically, a cardiologist may be required to make a significant number of small or incremental position adjustments and thus desires to have a favorable tactile response from the device. In other words, it would be highly desirable that the device have a rapid torque response. Accordingly, there is a need for elongated tubular devices such as guide wires and catheters that have a high degree of flexibility, rigidity and torquability for steerage.

SUMMARY OF THE INVENTION

The highly flexible tubular device for medical use of the present invention overcomes the limitations of the prior art devices in that it has a rapid torque response with a high degree of flexibility as set forth above.

In accordance with one aspect, the present invention is directed to an elongated torque tube for use in medical applications, comprising an elongated tubular structure having a cylindrical cross section and defining a longitudinal axis and a circumferential axis, the elongated tubular structure including a helical cut with a predetermined pitch or multiple varied pitches and having a finite thickness and extending along at least a portion of the length of the elongated tubular structure, the helical cut being oriented substantially along the circumferential axis and including a plurality of flexural units defined by discontinuous cuts substantially aligned with the circumferential axis.

In accordance with another aspect, the present invention is directed to an elongated torque tube for use in medical applications, comprising an elongated tubular structure having a cylindrical cross section and defining a longitudinal axis and a circumferential axis, the elongated tubular structure including a helical cut with a predetermined pitch or multiple predetermined varied pitches and having a finite width and extending along the length of the elongated tubular structure, the helical cut being oriented substantially along the circumferential axis and including a plurality of flexural units defined by discontinuous cuts substantially aligned with the circumferential axis. The flexural units, located at a predetermined spacing or multiple varied spacings down the length of the helical cut, comprise of a defined width or multiple, varied defined widths.

The present invention may be utilized in conjunction with any type of medical device where there is required a balance between flexibility, high initial one-to-one torque control, kink resistance, compression/buckling resistance and tensile strength. For example, guide wires and catheters as well as catheter components may be made in accordance with the present invention.

Essentially, an elongated rigid tube may be machined to include cuts therein that increase the flexibility of the device, thereby allowing the structure to be navigated through tortuous pathways. By increasing the flexibility through the use of helical cuts, torque control is diminished. Torque control or response or immediate torque response is diminished because of the finite thickness of the cuts. No device may be machined with a cut not having a finite thickness corresponding to the material removed. Accordingly, if the device is torque at one end, the gaps caused by the cut have to be filled in before there is rotational movement at the second ends. The present invention utilizes novel cutting configurations that provide both high flexibility and high initial torque response.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1 is a diagrammatic representation of an elongated tubular structure having a continuous helical cut there through.

FIGS. 4A-4C are a diagrammatic representation of an elongated tubular structure having a third discontinuous cut there through and details in accordance with the present invention.

FIGS. 5A-5D are diagrammatic representations of a various cut patterns that may be utilized in connection with the device illustrated in FIG. 4.

DETAILED DESCRIPTION OF THE PREFERRED EMBODIMENTS

Figure 1:
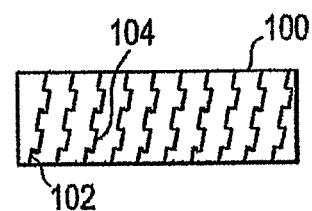

The present invention relates to highly flexible tubular devices with an initial or immediate substantially one-to-one torque ratio for medical use. The highly flexible tubular devices may comprise a catheter, a catheter sheath, a catheter shaft, a guide wire, an embolic coil and/or any combination thereof. While the highly flexible tubular devices may comprise any of these elements alone or in combination, for ease of explanation the following discussion shall focus on a generic elongated tubular device, wherein flexibility as well as other attributes is required, for example, for use in the vasculature as an interventional tool.

It is known in the field of interventional devices, that a high degree of flexibility with limited compromise in all functional areas is the key to success. However, with an elongated tubular device, an increase in flexibility generally means a lower initial or immediate torque transmission efficiency, for example, less than one-to-one. A rigid tube would have the highest immediate torque transmission efficiency. What this means is that any incremental rotational or twisting movement at the first end of the device will result in the same amount of rotational or twisting movement at the second end of the device with minimal or no loss, or a one-to-one torque correspondence. The response is immediate because as the first end is turned, the second end turns immediately because the tube is rigid. A flexible tube, such as a tube fabricated from a soft polymeric material would have low initial torque transmission efficiency. In this scenario, any incremental rotational or twisting movement at the first end of the device will be greater than the rotational or twisting movement at the second end of the device initially. Rotational or twisting movement is less at the second end due to the losses along the length of the elongated device. Accordingly, additional rotational or twisting movement at the first end is required to achieve the desired effect at the second end. Eventually, there will always be a one-to-one torque transmission efficiency as slop is removed as is explained in detail subsequently In accordance with one exemplary embodiment, a solution to the initial or immediate torque transmission efficiency and flexibility balancing problem would be to create helical cuts with a pattern along the length of an elongated rigid tube. The helical cuts would increase the flexibility of the tube; however, the torque transmission efficiency would be less than one hundred percent due to the thickness of the cuts or gaps that exist along the length of the elongated tube. The helical cut would preferably have a predetermined pitch or multiple predetermined varied pitches. The predetermined pitch or pitches are determined by specific desired design goals. Regardless of how the elongated tube is machined, the tool or laser utilized to cut the helical line has a certain finite thickness like that of the blade of a saw. In the case of a laser, the cut width or kerf would create the gap. Accordingly, when the first end of the elongated tube with helical cuts is rotated or twisted, before the second end of the elongated tube rotates, the material forming the tube will deform to fill in the gaps created by the cuts thereby creating a lag in movement at the second end. This lag may be referred to as "slop" in the rotational or twisting movement. Therefore, while the flexibility is increased, the torque transmission efficiency is less than one hundred percent.

Referring to FIG. 1, there is illustrated an elongated tube 100 comprising a helical laser cut pattern 102. It is important to note that the pattern could comprise any suitable pattern. For example, the helical cut 102 may comprise undulations 104. These undulations provide a docking mechanism such that as the device is twisted, eventually the circumferentially aligned parts of the pattern will dock eliminating the propagation. What is critical in this exemplary embodiment is that there is a finite width of the continuous cut. In other words, the elongated tube 100 becomes more flexible at the expense of having an initial or immediate torque transmission efficiency less than one hundred percent or one-to-one. Circumferentially oriented cuts are required to achieve flexibility, while longitudinally oriented cuts have to be minimized to reduce slop. In this design, pulling on the elongated structure would cause it to stretch like a spring.

Essentially, for the present invention to work in the vasculature, which in all likelihood may assume tortuous paths, gaps as described above are preferably present to increase flexibility. Slop, as described above, is a result of the gaps that occur when the device is manufactured. Accordingly, as the device is rotated or twisted, the gaps along its length are either open or closed depending on the direction of rotation. Ideally, there would be no gaps; however, in light of the need for flexibility and current processing technologies this is not possible with this design.

Accordingly, in accordance with another exemplary embodiment, an elongated tubular device with an unsurpassed balance of the key attributes of flexibility, one-to-immediate one torque control, kink resistance, compression/buckling resistance and tensile strength is disclosed. As noted above, the design may be incorporated into any part of the catheter or wires discussed above. Depending on the required use of the device, the design may be tailored to individually optimize any of the key attributes without significant compromise of the others. What makes this possible is the decoupling of these key attributes by changing the helical cut along the length of the tubular structure to a series of cuts as illustrated in FIGS. 2A and 2B.

Figure 2A:
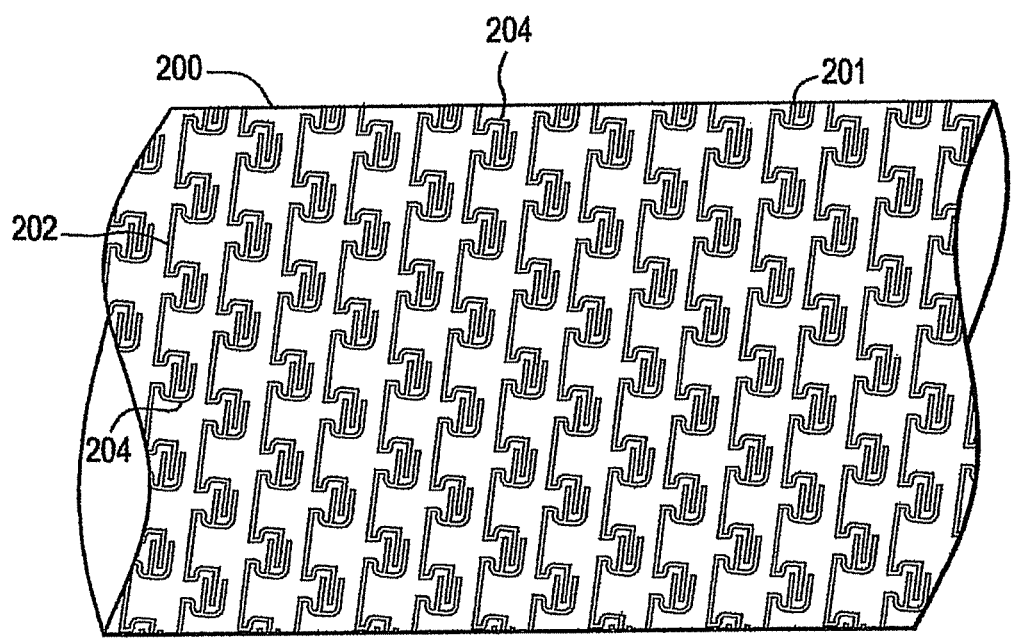
FIG. 2A is a diagrammatic representation of an elongated tubular structure having a first discontinuous cut there through in accordance with the present invention.

FIG. 2A illustrates a first exemplary embodiment of an elongated tubular structure 200 having a circular cross section defining a longitudinal axis and a circumferential axis comprising a cut 202 extending over at least a portion of the length of the structure 200 having discontinuous cuts or flexural units 204. With the discontinuities provided by the flexural units 204, even though there is a gap created in machining the cut 202, for example, the kerf width 201 as a result of laser processing, there is a significant increase in initial or immediate torque transmission efficiently, approaching one-to-one, while the decrease in flexibility over the length of the tubular structure 200 is only minimized slightly. The initial or immediate torque transmission efficiency is higher with the discontinuities because the discontinuities, which extend or align with the circumferential axis, allow the sections of the structure 200 to remain attached while the flexural units 204 allow to bend. As can be seen in FIG. 2A, the discontinuities in the flexural units are oriented along the circumferential axis. FIG. 2B illustrates a second exemplary embodiment of an elongated tubular structure 206 comprising a series of flexural units 208 on both sides of the circumferential cut which also has a kerf width 201 as a result of laser processing. This different design gives a different flexibility profile without any noticeable change in immediate torque response.

In the paragraph above, orientation is described with respect to being aligned with either or both the circumferential and/or longitudinal axis. However, in the actual design, the helical cut has a certain predetermined pitch or multiple predetermined varied pitches, as described above, and thus all cuts or designs described above are relative to this pitch or pitches. Accordingly, as used herein, orientation shall mean substantially aligned with a particular axis, only differing by the predetermined pitches.

Figure 2B:
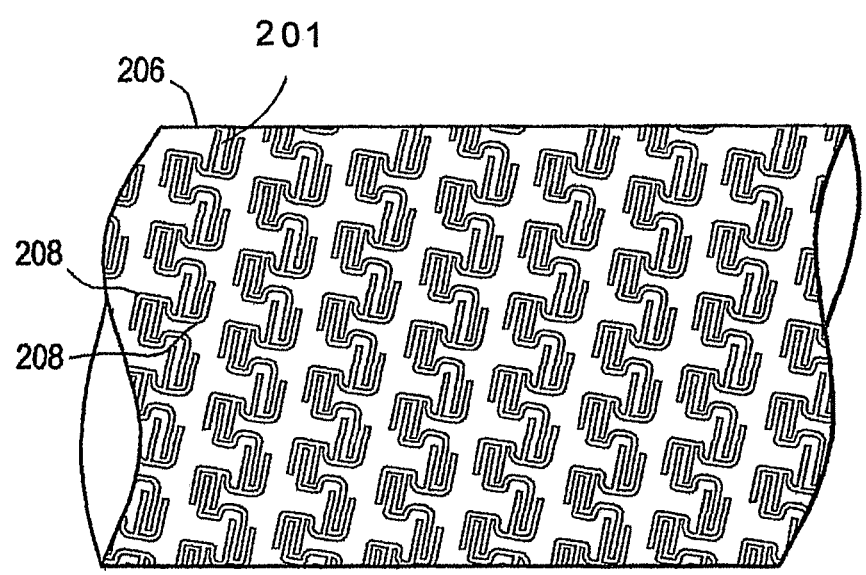
FIG. 2B is a diagrammatic representation of an elongated tubular structure having a second discontinuous cut there through in accordance with the present invention.

It is important to note that although the device illustrated in FIGS. 2A and 2B have exaggerated spacing 201 to better show the kerf width or cut spacing, the slop to be eliminated is the result of the total width of the kerf added up along the entire length of the device. In other words, while it appears that there are not a large number of patterned cuts both circumferentially and longitudinally because of the exaggerated kerf widths, there are in fact a significant number of patterned cuts on each device and this is what adds up to create the slop if it were not for the present invention.

Figure 2C:
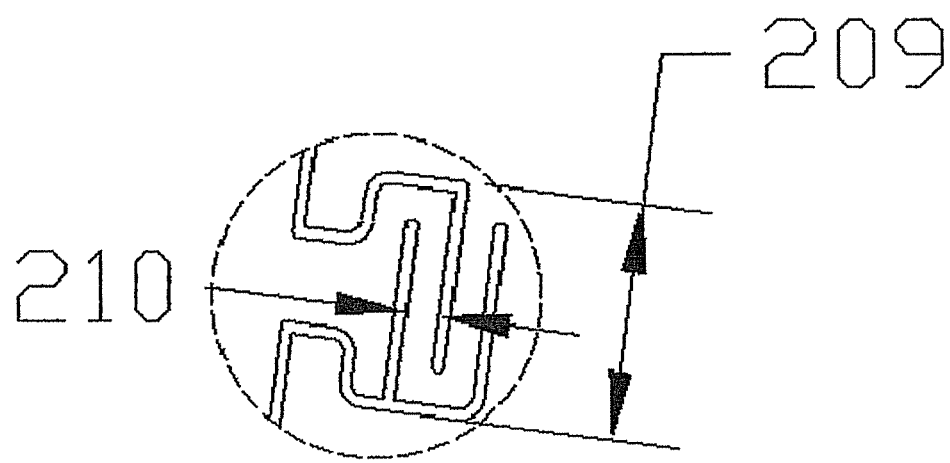
FIG. 2C is a detailed perspective of a portion of the device of FIG. 2A in accordance with the present invention.

It is also important to note that the flexural units can located at a single spacing down the helical cut pattern or can be located at different varied spacings down the helical cut pattern. It is also important to note that the overall width (209) of the flexural units can be a single width or varied widths. Further, the thickness (210) of each flexural strut can vary by design. This is illustrated in FIG. 2C.

Figure 3:
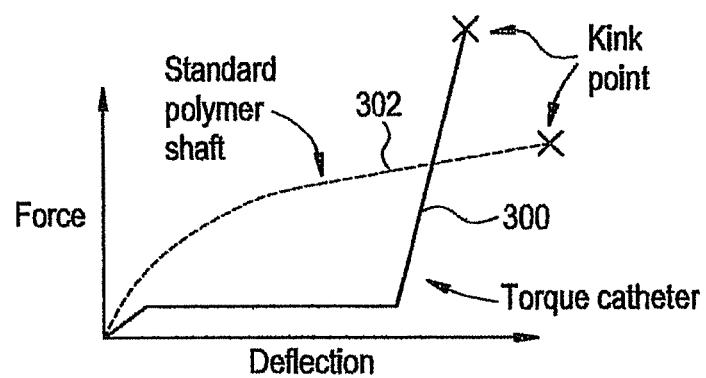
FIG. 3 is a representation of force deflection curves for elongated tubular structures in accordance with the present invention.

FIG. 3 illustrates the force deflection curves 300 and 302 for an elongated tube laser cut in accordance with the present invention as illustrated and described with respect to FIG. 2A versus a standard polymeric tube respectively. The standard elongated polymeric tube has a smooth force deflection curve 302 that requires more force to deflect initially and for a longer duration of deflection, whereas the elongated tube laser cut in accordance with the present invention is not a smooth curve 300, but initially requires less force to deflect and maintain deflection for a longer duration and then sharply increases beyond a certain point. Based upon the exact same pitch and number of interlocks, the main disadvantage is the slightly increased force to deflect, but the design is still more flexible than the standard polymeric tube. In other words, the force/deflection curve 300 for the tube cut in accordance with the present invention is much for flexible up to a certain point as compared to the standard polymeric tube as illustrated by curve 302. Essentially, to obtain the response shown by curve 300 with the cuts described herein, you would need an extremely pliable tube that has essentially zero torque control.

In accordance with another exemplary embodiment, the elongated tube may be machined utilizing a process that substantially eliminates at least a portion the gaps in the cut pattern. As described above, in order for this concept of a torque catheter and/or coil to work, axial gaps must be present for flexibility. These gaps are preferably created in the circumferential direction. Slop is a result of the opening and closing of the gaps that occur when the device is manufactured by a process such as laser cutting when the device is torqued. In this particular exemplary embodiment tabs are created in the cut line of the elongated tube along its length and are circumferentially oriented along the cut line. FIGS. 4A-4C illustrate this particular embodiment. FIG. 4A illustrates the larger tubular structure while FIGS. 4B and 4C illustrate specific details.

As is illustrated, the elongated tube 400 comprises a helical cut pattern 402 comprising tabs 404. As is illustrated in the detail bubbles, the helical cut pattern 402 comprising a series of lines are cut, typically with a laser, almost completely around the perimeter of the predetermined pattern. What makes this design unique is that the laser is turned off at certain points to create non cut regions, tabs or discontinuities 404. Accordingly, once all of the helical cut pattern 402 is cut in this manner, the tabs 404 may be broken at the weak non cut regions as part of a secondary process. The breaking of these tabs 404 creates a torque tube that is essentially free of slop because there is no gap caused by a cut in the longitudinal direction. The only gaps are in the circumferential direction; thereby allowing the device to flex, but have an immediate torque response. With a tab width 406 preferably greater than the kerf width 408, the possibility of both sides of the broken tabs 404 not touching would be eliminated, thus substantially eliminating the slop. By breaking the tabs 404, no cut line having a predetermined width is created.

The key to decoupling flexibility and torque response lies in the feature having a discontinuity 404, or tabs 404 as described above, substantially perpendicular to the circumferential cut line 409. Recalling that the circumferential cuts are required for flexibility, they cannot be eliminated from the device. However, a reduction in any cuts perpendicular to these circumferential cuts is desirable for eliminating slop, thereby increasing initial torque response.

In the paragraph above, orientation is described with respect to being aligned with either or both the circumferential and/or longitudinal axis. However, in the actual design, the helical cut has a certain predetermined pitch, as described above, and thus all cuts or designs described above are relative to this pitch. Accordingly, as used herein, orientation shall mean substantially aligned with a particular axis, only differing by the predetermined pitch.

It is important to note that although the device illustrated in FIGS. 4A, 4B and 4C have exaggerated spacing 408 to better show the kerf width or cut spacing, the slop to be eliminated is the result of the total width of the kerf added up along the entire length of the device. In other words, white it appears that there are not a large number of patterned cuts both circumferentially and longitudinally because of the exaggerated kerf widths, there are in fact a significant number of patterned cuts on each device and this is what adds up to create the slop if it were not for the present invention.

It is important to note that some slop will always be present as it is required to allow for free movement and axial bending. Slop deals with the opening and closing of the circumferential gaps and not the inherent elastic properties of the material once the gap has closed.

Essentially, in this design, by creating the non-cut regions or tabs 404 and then breaking the tabs 404 utilizing a secondary process, there is no gap created in the non-cut regions 404. No gap, no slop transmitted from these regions along the length of the device.

FIGS. 5A-5D illustrate various different exemplary embodiments for this design. For simplicity, no kerf widths are illustrated. FIG. 5A illustrates the design described above. FIG. 5B illustrates a design wherein tabs 410 are added to the head of the T-shaped cut pattern. FIG. 5C illustrates staggered tabs 412 along the shank of the T-shaped cut pattern to allow for greater axial travel. FIG. 5D is similar to the design of FIG. 5A but with beveled edges 414 on the head of the T-shaped cut pattern.

In each of the exemplary embodiments set forth and described above, the machining of the cuts was accomplished utilizing a laser and thus the width of each cut was referred to as a kerf width. These widths can be very narrow and thus the explanation on the additive effect. It is, however, important to note that any suitable cutting tool, for example, wire electro discharge machining, water jet machining and etching processing, may be utilized to create the patterns, and thus the present invention is not limited to the laser cut embodiment.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An elongated torque tube for use in medical applications, comprising an elongated tubular structure having a cylindrical cross section and defining a longitudinal axis and a circumferential axis, the elongated tubular structure including a discontinuous helical cut with at least one of a predetermined pitch or multiple predetermined varied pitches and having a finite width and extending along at least a portion of the length of the elongated tubular structure, the discontinuous helical cut being oriented substantially along the circumferential axis and including a plurality of flexural units, each flexural unit being offset from the helical cut along the longitudinal axis in a perpendicular direction from the helical cut, the flexural unit being defined at least in part by a first, second, and third cut, parallel to one another and the helical cut and spaced apart in the perpendicular direction from the helical cut to form a first flexural strut between the first and second cut, and a second flexural strut between the second and third cut at a single spacing or varied spacing consisting of a single overall width or multiple varied widths.

2. The elongated torque tube according to claim 1, wherein the plurality of flexural units comprise a series of cuts in alignment with both the circumferential axis and the longitudinal axis.

3. The elongated torque tube according to claim 2, wherein the series of cuts have at least one discontinuity in alignment with the circumferential axis.

4. The elongated torque tube according to claim 3, wherein the series of cuts have at least one discontinuity in alignment with the longitudinal axis.

5. The elongated torque tube according to claim 1, wherein the elongated torque tube comprises a guide wire.

6. The elongated torque tube according to claim 1, wherein the elongated torque tube comprises a catheter sheath.

7. The elongated torque tube according to claim 1, wherein the elongated torque tube comprises a catheter shaft.

8. The elongated torque tube according to claim 1, wherein the elongated torque tube comprises a catheter.

9. An elongated torque tube for use in medical applications, comprising an elongated tubular structure having a cylindrical cross section and defining a longitudinal axis and a circumferential axis, the elongated tubular structure including a helical cut with a predetermined pitch and having a finite thickness and extending along the length of the elongated tubular structure, the helical cut being oriented substantially along the circumferential axis and including a plurality of flexural units defined by discontinuous cuts aligned with both the circumferential axis and the longitudinal axis.

\* \* \* \* \*